United States Patent
Leahy

(10) Patent No.: US 8,915,967 B2
(45) Date of Patent: Dec. 23, 2014

(54) ANTI REFLUX SYSTEM

(76) Inventor: Patrick Leahy, Dublin (IE)

( * ) Notice: Subject to any disclaimer, the term of this patent is extended or adjusted under 35 U.S.C. 154(b) by 1809 days.

(21) Appl. No.: 10/596,600

(22) PCT Filed: Dec. 20, 2004

(86) PCT No.: PCT/EP2004/014572
§ 371 (c)(1), (2), (4) Date: Apr. 3, 2007

(87) PCT Pub. No.: WO2005/058210
PCT Pub. Date: Jun. 30, 2005

(65) Prior Publication Data
US 2007/0208429 A1  Sep. 6, 2007

(30) Foreign Application Priority Data
Dec. 19, 2003  (IE) .................. S2003/0954

(51) Int. Cl.
*A61F 2/04* (2013.01)
*A61F 2/00* (2006.01)
*A61F 2/02* (2006.01)
*A61F 2/24* (2006.01)

(52) U.S. Cl.
CPC ............ *A61F 2/0004* (2013.01); *A61F 2/02* (2013.01); *A61F 2/24* (2013.01); *A61F 2002/044* (2013.01)
USPC ........................................... 623/23.68

(58) Field of Classification Search
CPC  A61F 2/04; A61F 2002/044; A61F 2002/045
USPC ............ 606/108; 623/1.1, 1.11, 1.12, 1.24, 623/1.25, 1.26, 1.36, 1.39, 2.1, 2.11, 2.12, 623/3.1, 2, 900, 23.64–23.65, 23.67–23.68; 604/9
See application file for complete search history.

(56) References Cited

U.S. PATENT DOCUMENTS

| 4,846,836 | A  | * | 7/1989  | Reich .................. 623/23.68 |
| 5,314,473 | A  | * | 5/1994  | Godin .................. 623/23.68 |
| 5,861,036 | A  | * | 1/1999  | Godin .................. 623/23.64 |
| 6,007,575 | A  | * | 12/1999 | Samuels ................. 623/1.15 |
| 6,254,642 | B1 | * | 7/2001  | Taylor .................. 623/23.64 |
| 6,264,700 | B1 | * | 7/2001  | Kilcoyne et al. ........ 623/23.68 |
| 2001/0020190 | A1 | * | 9/2001 | Taylor ................... 623/23.68 |
| 2005/0075730 | A1 | * | 4/2005 | Myers et al. ............. 623/2.18 |
| 2007/0027518 | A1 | * | 2/2007 | Case et al. ............... 623/1.1 |

FOREIGN PATENT DOCUMENTS

WO    WO 03003949 A2 *  1/2003

* cited by examiner

*Primary Examiner* — Andrew Iwamaye
(74) *Attorney, Agent, or Firm* — Porter, Wright, Morris & Arthur, LLP

(57) ABSTRACT

The present invention is concerned with a system and method for preventing or substantially reducing the occurrence of gastroesophageal reflux in a human or animal, in particular by the fixation of a valve based device (10) within the stomach of such a human or animal, about the lower oesophageal sphincter muscle, which device supersedes the operation of said lower oesophageal sphincter muscle, in particular in situations when the lower oesophageal sphincter muscle is damaged.

12 Claims, 4 Drawing Sheets

ANTI REFLUX SYSTEM

The present invention is concerned with an anti reflux system, and in particular an anti reflux device comprised in the system, which device is adapted for location within the stomach of a human or animal, about the lower oesophageal sphincter muscle leading from the oesophagus into to the stomach. The present invention is also concerned with a method of treating acid reflux in a human or animal.

At some stage almost every person will experience indigestion or heartburn to some degree. Gastroesophageal reflux, the medical name for heartburn, is the condition in which stomach acid is regurgitated into the oesophagus, resulting in the burning sensation that can radiate into the throat. However, in a large number of individuals, gastroesophageal reflux is sufficiently frequent or severe such as to cause more significant problems, and is considered to be a disease, known as gastro-oesophageal reflux disease (GERD).

This disease occurs when the lower oesophageal sphincter muscle ceases to function normally, and for example is either weak or relaxes inappropriately when exposed to certain stimuli, such as particular food types, alcohol, exercise, or certain types of medication, allowing the liquid content of the stomach to reguritate (reflux) into the oesophagus. This liquid contains, among other things, acid produced by the stomach, and possibly bile produced in the duodenum, which has backed up into the stomach. However, the acid content of this stomach liquid caused the greatest damage and discomfort. GERD damages the lining of the oesophagus due to the present of this acid, resulting in considerable pain and inflammation. During the day, such reflux is significantly less damaging, as the oesophagus is protected by swallowing, saliva and the effect of gravity tending to cause the stomach acid to drain back into the stomach. In addition, saliva produced in the mouth contains bicarbonate, which acts to neutralise any acid remaining in the oesophagus following the actions of gravity and swallowing. However, while lying asleep at night, the effectiveness of the aforementioned protective mechanisms are significantly reduced, as gravity no longer drives the stomach liquid back into the stomach while the person is lying horizontally, swallowing stops during sleeping, and very little saliva is produced. Thus stomach acid is likely to remain in the oesophagus for prolonged periods, causing greater damage.

Although there are treatments available to reduce or prevent GERD, once these treatments are discontinued, the condition is extremely likely to return, and so for most sufferers, this condition is a life long one which is the cause of much discomfort and a resultant reduction in the quality of life.

The present invention therefore seeks to provide a system and method for providing a temporary or permanent replacement of a damaged lower oesophageal sphincter muscle, and in so doing to prevent or significantly reduced the occurrence of acid reflux.

The present invention therefore seeks to provide an anti reflux system, and in particular an anti reflux device which effectively replaces the lower oesophageal sphincter muscle, in order to prevent gastroesophageal reflux. The present invention further seeks to provide an anti reflux device which may remain operational for a prolonged period, in order to allow the lower oesophageal sphincter muscle to be repaired, whether naturally or by corrective surgery.

The present invention therefore provides, according to a first aspect, an anti reflux device comprising a valve arranged to allow unidirectional flow through the valve; and retention means adapted to enable the device to be secured to a wall of a human or animal stomach.

Preferably, the valve is substantially flexible.

Preferably, the valve is substantially collapsible.

Preferably, the valve comprises a mitral valve.

Preferably, the retention means comprises a flange disposed substantially circumferentially about the valve, which flange is adapted to enable the device to be secured to the stomach wall.

Preferably, the flange is provided with an adhesive on a stomach contacting face of the flange.

Preferably, the flange defines a conduit therein which is in fluid communication with the contacting face.

Preferably, the fluid communication between the conduit and the contacting face is provided by a plurality of apertures in the flange.

Preferably, the device is substantially biodegradable.

Preferably, the valve is adapted to permit the direction of the flow through the valve to be reversed when a predetermined threshold pressure within the stomach is reached.

The present invention also provides, according to a second aspect, an anti reflux system comprising a device according to the first aspect of the invention; and positioning means adapted to position the device against the stomach wall while the device is being secured to said stomach wall.

Preferably, the positioning means comprises a distensible element adapted to clamp the device between the stomach wall and the distensible element.

Preferably, the positioning means comprises a tether detachably engageable with the distensible element, to allow the distensible element to be drawn against the stomach wall.

Preferably, the distensible element is an inflatable balloon.

Preferably, the system further comprises dispensing means detachably connectable, in fluid communication, with the device, the dispensing means being operable to pump an adhesive onto the flange.

Preferably, the system further comprises insertion means adapted to facilitate the insertion of the device into the stomach.

Preferably, the insertion means comprises an elongate tube adapted to receive the device, in a collapsed state, and from which tube the device may be dispensed into the stomach.

The present invention further provides, according to a third aspect, a method of treating gastroesophageal reflux comprising the steps of; locating a unidirectional flow valve device in the stomach of a human or animal; and securing the valve device to a wall of the stomach, about the oesophageal sphincter muscle, and in an orientation permitting the unidirectional flow through the valve into the stomach.

Preferably, the method comprises, in the step of locating the valve device in the stomach, collapsing the valve device and passing the valve device through the oesophagus and into the stomach.

Preferably, the method comprises, in the step of locating the valve device, collapsing the valve device about a distensible element, passing the valve device and the distensible element through the oesophagus and into the stomach, and distending the distensible element in order to deploy the valve device.

Preferably, the method comprises, in the step of securing the valve, providing an adhesive on a stomach wall contacting portion of the valve device, and urging the contacting portion against the stomach wall until the adhesive has substantially adhered to the stomach wall.

Preferably, the method comprises, in the step of securing the valve device, drawing the distensible element against the stomach wall following the distension thereof, and retaining the distensible element in said position until the valve device is substantially secured to the stomach wall.

Preferably, the method comprises, in the step of distending the distensible element, inflating the distensible element.

Preferably, the method comprises, in the step of applying the adhesive, pumping the adhesive onto the contacting portion from outside the stomach.

As used herein, the term "unidirectional" is intended to mean flow in one direction only, but more particularly in only one direction under normal operating conditions, which direction of flow may however be reversed if normal operating conditions are exceeded.

As used herein, the term "mitral valve" is intended to mean a valve which, during normal operation, is a non-return or unidirectional valve which may for example be formed from a flexible tube having an inlet and an outlet. The inlet is held permanently open by any suitable means, for example by securing to a flange or the like, while the outlet is freely suspended, for example within a stomach of a human or animal. In this way the valve will enable the flow of material therethrough when the pressure is either the same between the inlet and the outlet or when the pressure is higher at the inlet compared to the outlet, for example during swallowing, while the tube will collapse on itself when the pressure is higher at the outlet, thereby closing the valve. It is also possible that the flexible tube could be replaced with two or more leaflets which are deformable away from one another to permit flow in one direction, a forward direction, through the valve, and which collapse against one another when the flow is reversed, in order to prevent such reversed flow through the valve.

As used herein, the term "distensible" is intended to mean the ability to distend or expand/deform/displace outwardly in order to be capable of generating or producing a larger contact area for applying pressure to another object or element, and may be achieved by inflation, mechanical displacement, or by any other suitable means.

As used herein, the term "inflation" is intended to mean the act of inflating an object with a fluid, whether with a gas or a liquid.

The present invention will now be described with reference to the accompanying drawings, in which.

Figure 1:
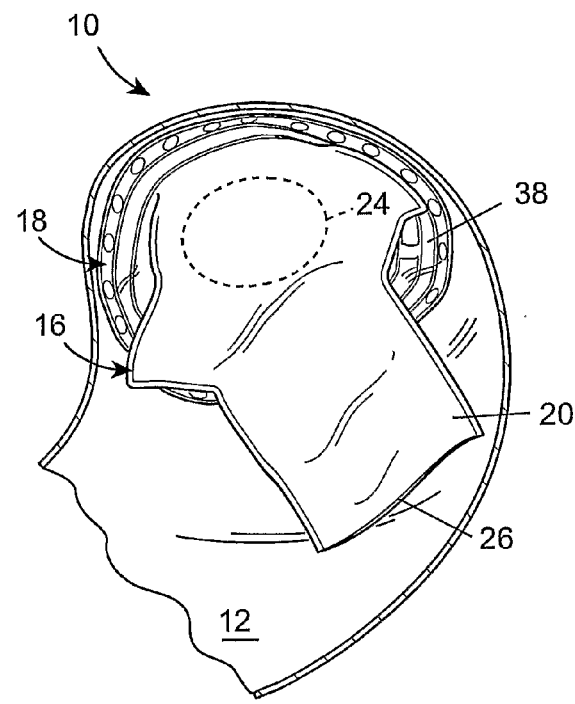
FIG. 1 illustrates a perspective view of an anti reflux device forming part of an anti reflux system according to the present invention, in which the device is in a closed state, secured to a wall of a human or animal stomach.

Referring now to the accompanying drawings, there is illustrated an anti reflux system comprising an anti reflux device, generally indicated as 10, which, in use, prevents or significantly reduces the reflux of stomach content, in particular liquid content containing stomach acid, and is intended for particular application where the lower oesophageal sphincter muscle (not shown) has ceased to function correctly. The device 10 is located, in use, in a stomach 12 of a human or animal patient (not shown), at and about the entrance from an oesophagus 14. The device 10 is therefore seated adjacent and about the lower oesophageal sphincter muscle (not shown), and supersedes the operation of same while the device 10 is in place, as will be described in detail hereinafter.

The device 10 is preferably formed from a flexible biodegradable material, for example a biodegradable medical grade polymer as manufactured by Dow of Michigan, the United States, which may be chosen such that the device 10 will at least substantially biodegrade after a pre-determined period, for example 6 to 12 months after the insertion of the device 10. The working life of the device 10 is therefore preferably chosen to suit the needs of the individual patient, in particular the length of time expected for the damaged lower oesophageal sphincter muscle (not shown) to repair, whether naturally or with the aid of suitable medication or surgery. It is of course possible that the device 10 be formed form a non-biodegrading material, for example a medical grade polyurethane as manufacture by Dow of Michigan, the United States, in particular if a patient's lower oesophageal sphincter muscle is unlikely to repair itself, in which case the device would permanently replace the functioning thereof.

The device 10 comprises a valve 16 depending from retaining means in the form of a flange 18, which flange 1 8 is adapted to enable the device 10 to be adhered to a wall of the stomach 12, as will be described in greater detail hereinafter, about the lower oesophageal sphincter muscle, such that any material passing from the oesophagus 14 into the stomach 12 must pass through the device 10. The valve 16 is adapted to permit, under normal operating conditions, unidirectional flow from the oesophagus 14 into the stomach 12, and to prevent the reflux of stomach fluid/acid into the oesophagus 14. In the preferred embodiment illustrated, the valve 16 is a mitral valve, although it will be appreciated that any other suitable equivalent may be used in place thereof. However, the configuration of the valve 16 gives simple yet highly effective operation, in addition to allowing reversal of flow therethrough upon a threshold pressure being reached within the stomach 12, for example during vomiting, as will be described hereinafter. The simple configuration and operation of the device 10, and in particular the valve 16, is an important and desirable aspect of the present invention, as the device 10 is located, in use, within a human or animal patient, and provides an important biological function. Thus the simplicity of the device 10 reduces the likelihood of a malfunction thereof, which is obviously desirable due to the relative inaccessibility of the device 10 in the event that repairs are required thereto, in addition to the consequences to the patient of a malfunction of the device 10.

The valve 16 comprises a first side 20 and a second side 22, formed from a flexible material such as plastic or the like, which sides 20, 22 thus define a flexible tube. Each of the sides 20, 22 is sealed to the flange 18, about an inlet in the form of a central aperture 24 in the flange 18. The sides 20, 22 are also sealed along the edges thereof, while being left open at an outlet in the form of a mouth 26, oppositely disposed the central aperture 24, thereby defining a passage through the valve 16. The sides 20, 22 are preferably sealed together at their edges, and to the flange 18, by plastic welding, although any other suitable method may be used to effect this sealing. It will also be appreciated that the sides 20, 22 could be formed integrally with one another, so avoiding the need to seal the edges together.

Figure 2:
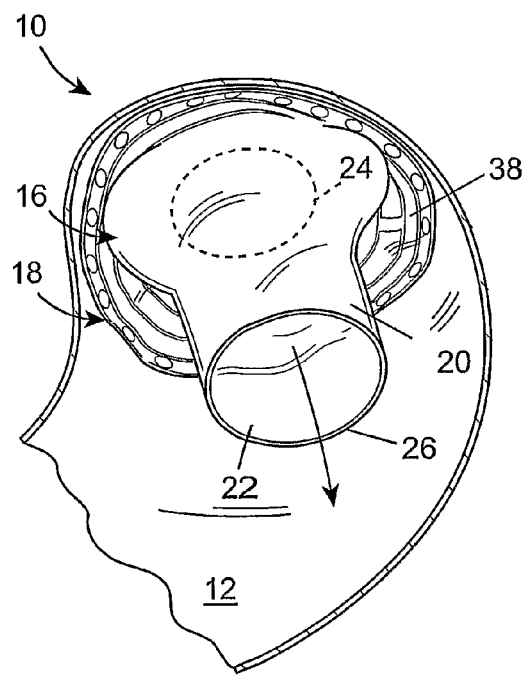
FIG. 2 illustrates the anti reflux device of FIG. 1, in an open state, allowing passage into the stomach.

The configuration of the valve 16 is such that it has two modes of operation, as illustrated in FIGS. 1 and 2 respectively. In FIG. 1, the valve 16 is shown in a closed state, in which nothing is being consumed/swallowed by the individual, and so the stomach 12 should be sealed from the oesophagus 14. In the preferred embodiment illustrated, where the valve 16 is in the form of a mitral valve, the natural pressure within the stomach 12, which is normally higher than the pressure within the oesophagus 14, forces the sides 20, 22 to collapse flat against one another, shutting the mouth 26, and therefore preventing the reflux of stomach liquid/acid into the oesophagus 14.

Referring now to FIG. 2, once an item of food (not shown) or the like is swallowed, the item passes down the oesophagus 14 towards the entrance to the stomach 12, and reaches the device 10. Peristalsis within the oesophagus 14 increases the pressure within the oesophagus 14 to a level above that of the stomach 12, and so forces the item through the central aperture 24, between the sides 20, 22, thereby forcing open the mouth 26 due to the flexible nature of the valve 16. Thus the item passes through the valve 16 safely into the stomach 12. Once passed, the mouth 26 is again forced closed due to the drop in pressure within the oesophagus 14, which results in a positive pressure within the stomach 12, sealing the valve 16 and therefore sealing the stomach 12 to prevent or substantially reduce reflux therefrom. The flexibility of the valve 16 prevents any food items from becoming lodged therein, thus ensuring the safe operation of the device 10. Thus although it is envisaged that the valve 16 could be replaced with a rigid or semi-rigid functional equivalent, it will be appreciated that the flexible nature of the valve 16 is preferred.

It will also be appreciated that there are times when it may be necessary to allow pressure within the stomach 12 to be released, for example during vomiting or belching. The valve 16, together with the central aperture 24, is suitably flexible such that on a threshold pressure being reached within the stomach 12, the valve 16 will be temporarily forced inside out, thereby enabling pressure to be vented into the oesophagus 14. When this occurs, the valve 16 is inverted, being forced up through the central aperture 24, to project into the oesophagus 14, wherein the mouth 26 can then open to allow the stomach contents to pass into the oesophagus 14. Once the pressure within the stomach 12 has returned to normal, and in combination with the normal swallowing action, the valve 16 will be forced back through the central aperture 24 into the normal configuration, to again seal the stomach 12 from the oesophagus 14. It will thus be appreciated that, although as mentioned throughout the description of the operation of the device 10, the valve 16 is described as allowing unidirectional flow, this is only under normal operating conditions, and in exceptional circumstances, the valve 16 can allow the reversal of flow therethrough.

A number of approaches may be employed, whether together or in isolation, in order to provide this reversible functionality to the valve 16. For example, the material chosen to form the valve 16, or the thickness of said material, may be selected to give a sufficient degree of rigidity to the valve 16, while maintaining suitable flexibility to function as hereinbefore described, so that the valve 16 will only reverse or invert when a predetermined pressure is reached within the stomach 12. These parameters will change depending on the size of the device 10, and in particular the valve 16, which may vary depending on the patient to which the device 10 is to be fitted. Thus a choice on the material to be used for the valve 16, or the thickness of the material, is a simple matter of trial and error experimentation.

Another parameter which may be varied in order to vary the threshold pressure at which the valve 16 will invert is the longitudinal length of the valve 16. The greater the length of the valve 16, the greater will be the resistance to the inversion of the valve 16. Thus the length of the valve 16 may be chosen to suit a particular application of the device 10, again using a simple process of trial and error experimentation to determine the requisite length.

In the preferred embodiment illustrated, in order to affix the device 10 to the stomach 12, a layer of adhesive (not shown), preferably a biocompatible adhesive, for example Bioglue® as manufactured by Cryolife Inc, of Georgia, the United States, is provided on a stomach contacting or upperside of the flange 18, as will be described in more detail hereinafter, thereby providing a quick and effective means of securing the device 10 to the stomach 12. There are however a number of other ways in which the device 10 could be located and secured in position within the stomach 12. One method would be to cut an incision in the stomach 12 from the exterior, and to then press the device 10 into place by hand, applying pressure until the adhesive on the flange 18 is suitably set. Alternatively, the device 10 could be sutured into place, possibly with dissolvable/biodegradable stitching or the like being passed through the flange 18 into the wall of the stomach 12. The stomach 12 would then have to be stitched closed, in addition to the entry incision in the abdomen (not shown). However, such a method is both time consuming, costly, and involves a significant recovery period for the patient. In addition, the conventional complications associated with such surgery, such as infection, rupturing of the incisions, etc., may arise.

Figure 3:
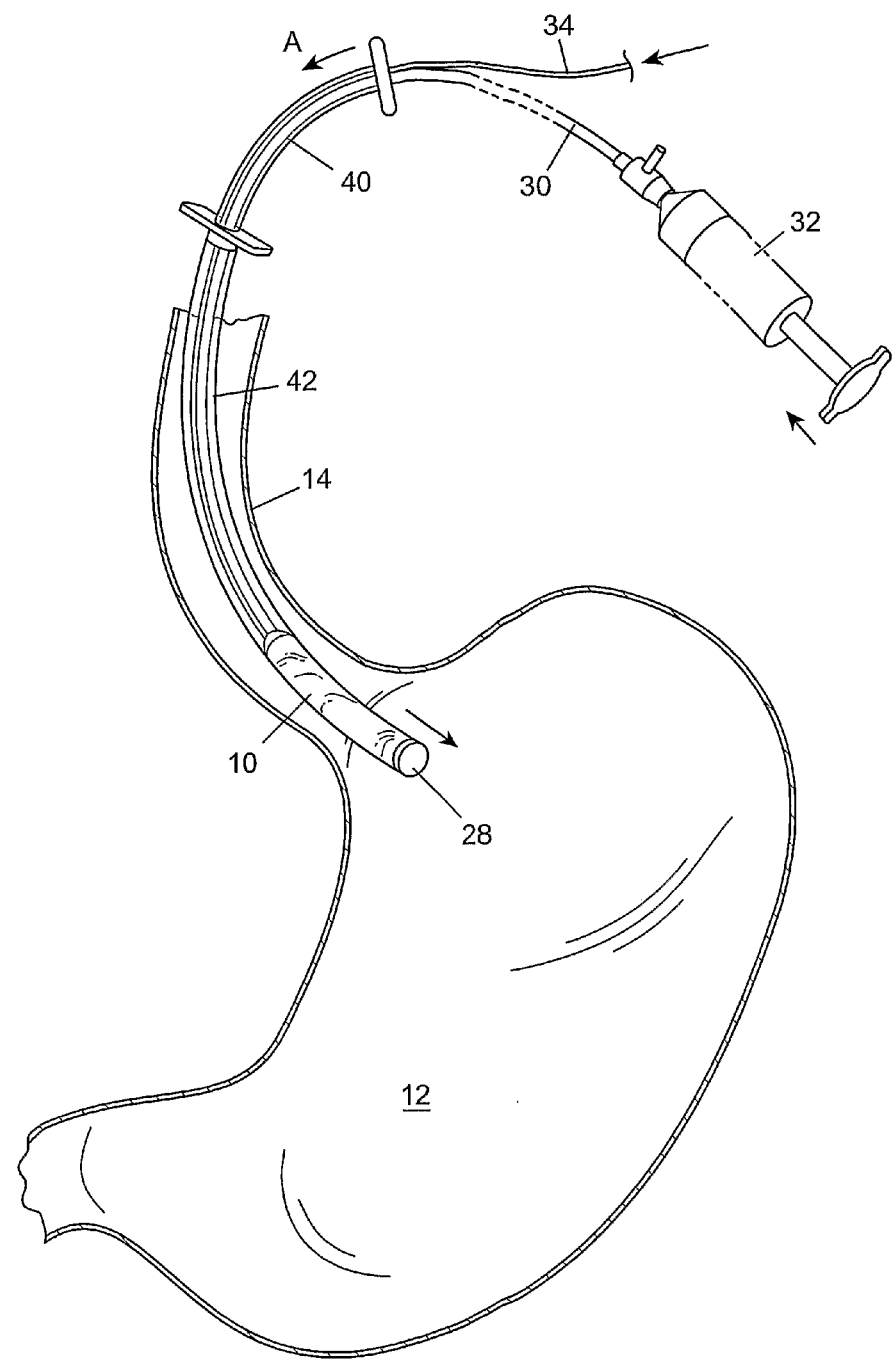
FIG. 3 illustrates a perspective view of the anti reflux device, in a collapsed state, being passed down the oesophagus and into the stomach.
Figure 4:
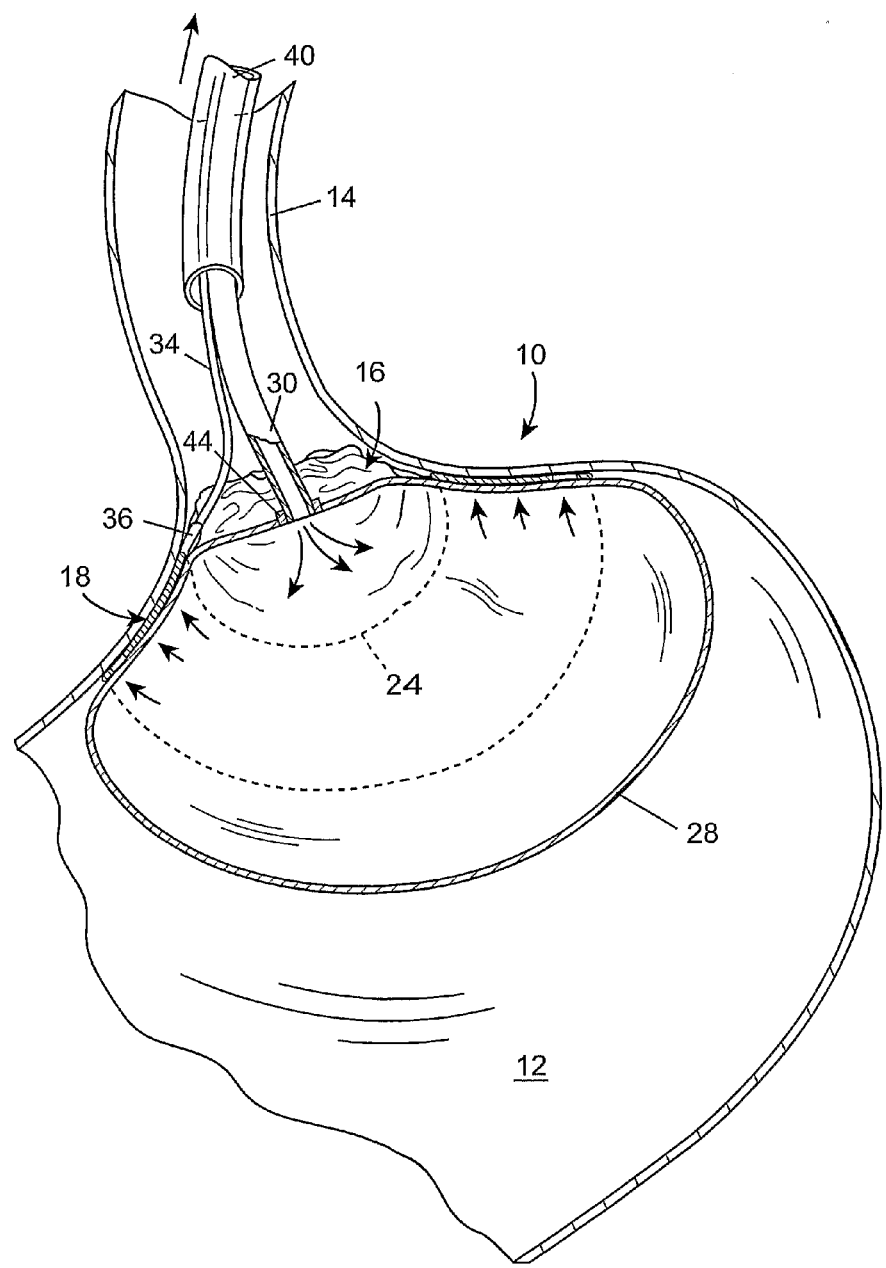
FIG. 4 illustrates the anti reflux device being pressed against the stomach wall by a balloon inflated adjacent thereto.

Thus, referring to FIGS. 3 and 4 of the accompanying drawings, the present invention also provides a method for inserting and securing the device 10 in place, which does not require any surgical incisions to be made.

The method comprises inserting the device 10 through the oesophagus 14 and into the stomach 12, wherein the device 10, preferably having the adhesive on the flange 18, is drawn against the stomach 12, in order to affix same in place by virtue of the adhesive covered flange 18. In order to effect this method of insertion, the anti reflux system of the present invention further comprises positioning means, in particular a distensible element in the form of an inflatable balloon 28, which in use is seated against the underside of the flange 18, with an inflating tube 30 being passed through the central aperture 24 of the valve 16, and detachably connected to the balloon 28. The inflating tube 30 is connected, in use, to a syringe 32 at an opposed end of the tube 30, which syringe 32 is then operable to inflate the balloon 28, as will be described. It will however be appreciated that any other means may be provided in order to inflate the balloon 28.

Prior to being connected to the syringe 32, the inflating tube 30 is passed first through a feed tube 40, formed from plastic or any other suitable material, which feed tube 40 is located within insertion means in the form of an applicator tube 42, again being formed from plastic or the like, the feed tube 40 being slideable within the applicator tube 42. An adhesive tube 34 is also provided, forming part of the anti reflux system, and running parallel to the inflating tube 30, which also passes through both the feed tube 40 and the applicator tube 42. The adhesive tube 34 is connected to a sleeve 36, projecting from the flange 18, which sleeve 36 is in fluid communication with a conduit in the form of an annular channel 38 defined by and within the flange 18. The annular channel 38 is provided with a plurality of minute apertures (not shown) opening onto the upper side of the flange 18, such that the channel 38 is in fluid communication with the upper side of the flange 18. Thus, in use, a suitable adhesive (not shown) may be pumped down the adhesive tube 34, around the annular flange 38, to seep out of the apertures (not shown), thereby providing a layer of adhesive onto the flange 18, to enable the device 10 to be adhered in place.

Thus, referring to FIG. 3, in order to insert the device 10 into the stomach 12, the balloon 28, deflated, is located beneath the device 10, both of which are then preferably furled or wrapped into a substantially cylindrical form, and seated against the free end of the feed tube 40. The applicator tube 42 is then slid down over the device 10 and balloon 28, in order to enclose same and retain the device 10 and balloon 28 in their collapsed state. The feed tube 40 and applicator tube 42 are then passed down the oesophagus 14, until the end of applicator tube 42 reaches the stomach 12. At this point, the applicator tube 42 is held in place, and the feed tube 40 slid further, in the direction of arrow A, thereby forcing the device 10 and balloon 28 out of the applicator tube 42 and into the stomach 12.

Figure 5:
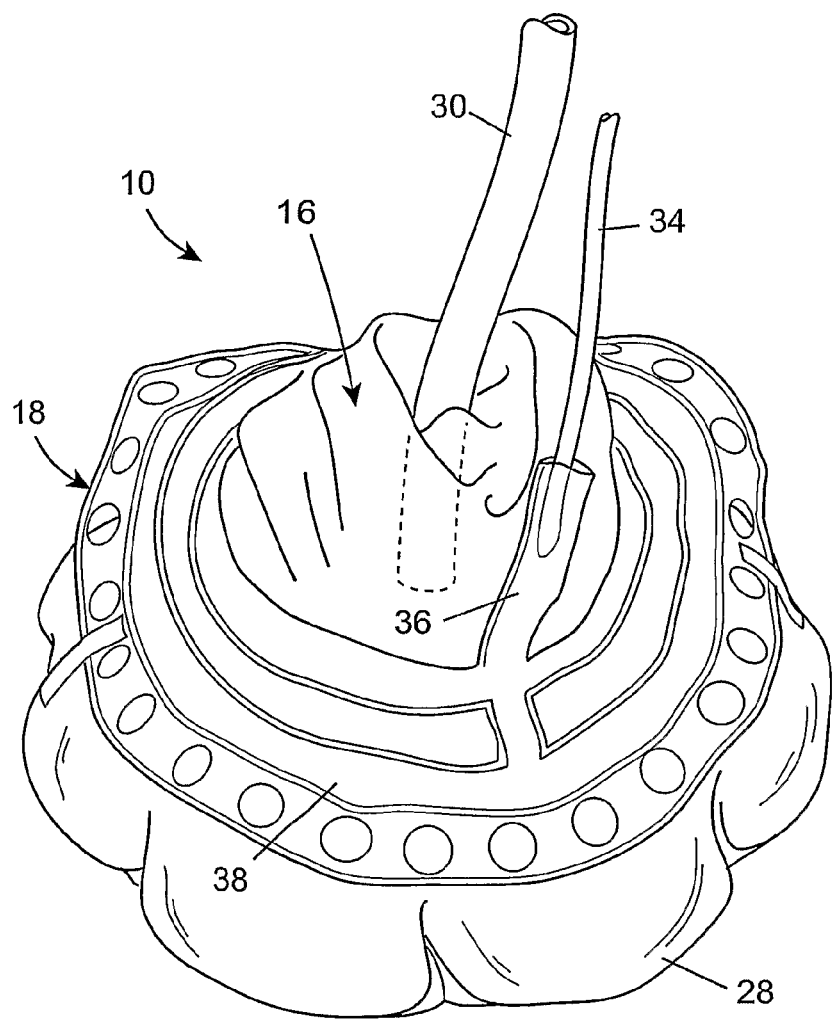
FIG. 5 illustrates a perspective view of the anti reflux device of the invention, in isolation from the stomach, with the balloon of FIG. 4 inflated therebeneath.

At this point, the balloon 28 is inflated, thereby causing the device 10 to unfurl or be deployed into a working configuration, assuming the configuration illustrated in FIG. 5. Once the balloon 28 is fully inflated, the preferably biocompatible adhesive (not shown) is pumped, from outside the patient's body, into the annular channel 38, and therefore seeps out onto the upper side of the flange 18. The adhesive may be pumped through the adhesive tube 34 by any suitable means, for example from a syringe (not shown) or the like. The adhesive is then left for a short period, in the embodiment illustrated approximately 30 seconds, in order to allow same to begin to cure. Following this short interval, the balloon 28 is drawn against the stomach 12, as illustrated in FIG. 4, by pulling on the inflating tube 30, which thus acts as a tether to the balloon 28, allowing same to be manipulated from outside the patient's body. This urging of the balloon 28 against the stomach 12, with the device 10 trapped therebetween, acts to press the adhesive covered flange 18 against the stomach 12, with the central aperture 24 being aligned with the opening to the oesophagus 14, the pressure being maintained until the adhesive on the flange 18 is sufficiently cured to secure the device 10 in place.

The balloon 28 is then detached from the inflating tube 30 by means of a collar 44, which effects separation of the balloon 28 from the inflating tube 30 upon a threshold pressure being reached within the balloon 28, which in the embodiment illustrated is achieved when the volume of the balloon 28 reaches approximately 500 cc. Thus in practice once the flange 18 has been suitably secured to the stomach 12, the balloon 28 is further inflated to reach this threshold pressure/volume, following which the balloon 28 then separates from the collar 44. It will of course be understood that any other suitable arrangement or mechanism may be employed in order to enable the balloon 28 to be disconnected from the inflating tube 30, for example by utilising some form of spring loaded clip (not shown) which is remotely operable, preferably from outside the patient's body.

The inflating tube 30 is then retracted, and the balloon 28 deflates, dropping into the stomach 12 to harmlessly degrade. For this reason the balloon 28 is preferably formed from a biodegradable material. Alternatively, the balloon 28 may be withdrawn back through the oesophagus 14, in a deflated state, by any suitable means, for example a cannula (not shown) or the like. The feed tube 40, applicator tube 42, inflating tube 30 and adhesive tube 34 are then withdrawn from the oesophagus 14, leaving the device 10 secured in place within the stomach 12. The device 10 then remains secured in place for a pre-determined period of time, in order to allow the lower oesophageal sphincter muscle (not shown) to repair, or alternatively to be repaired by surgery or medication. It will however be appreciated that a more permanent form of the device 10 could be provided, in order to replace the functioning of a permanently damaged lower oesophageal sphincter muscle (not shown).

It is also envisaged that the device 10 could be secured to the stomach 12 by means other than the adhesive covered flange 18. For example, some form of barbs (not shown) or similar flesh engaging hooks or fasteners (not shown) could be employed in order to fasten the device 10 to the stomach 12. Indeed such fasteners could be positioned on the stomach contacting face of the flange 18, to be pressed into engagement with the stomach 12, thereby replacing the requirement for an adhesive to be pumped onto the flange 18. Alternatively, a coating of adhesive could be applied to the flange 18 prior to inserting the device 10 into the stomach 12, for example during the manufacture of the device 10, possibly with the addition of a removable or dissolvable cover or film (not shown) being provided over said layer of adhesive.

It will therefore be appreciated from the foregoing description that the system and method of the present invention provide a simple yet effective means of eliminating or substantially reducing gastroesophageal reflux, in particular in situations where the lower oesophageal sphincter muscle is defective or damaged in any way.

The invention claimed is:

1. An anti reflux system comprising:
   an anti reflux device, the anti reflux device comprising:
      a valve having an inlet at a proximal end and an outlet at a distal end, the valve defining an axially extending passage arranged to allow unidirectional flow through the passage through the valve from the inlet to the outlet;
      retention means adapted to enable the anti reflux device to be secured to a wall of a human or animal stomach, wherein the retention means comprises a flared radially extending flange disposed circumferentially about the valve, the flange comprising a conduit defined by and within the flange, the conduit being a radially extending annular channel, the annular channel having a plurality of apertures opening onto a stomach contactable side of the flange, the plurality of apertures being circumferentially spaced-apart along the flange about the valve;
      the inlet of the valve being within the flange and the outlet of the valve being suspended distal to the flange;
   an adhesive; and
   a dispensing means sized to extend from outside of a patient's body to the patient's lower esophageal sphincter, the dispensing means comprising a tube and a syringe detachably connectable and in fluid communication with the anti reflux device, the dispensing means being operable to pump the adhesive into and through the annular channel and around the valve to seep out of the plurality of apertures and onto the stomach contactable side of the flange to provide a layer of the adhesive on the stomach contactable side of the flange and enable the anti reflux device to be secured to the stomach wall.

2. An anti reflux system according to claim 1 wherein the valve is flexible.

3. An anti reflux system according to claim 1 wherein the valve is collapsible.

4. An anti reflux system according to claim 1 wherein the valve comprises a mitral valve.

5. An anti reflux system according to claim 1 wherein the flange is provided with the adhesive on the stomach contactable side of the flange.

6. An anti reflux system according to claim 1 wherein the anti reflux device is biodegradable.

7. An anti reflux system according to claim 1 wherein the valve is adapted to permit a direction of a flow through the valve to be reversed when a predetermined threshold pressure within the stomach is reached.

8. An anti reflux system according to claim 1 further comprising positioning means comprising a distensible element adapted to position the anti reflux device against the stomach wall while the anti reflux device is being secured to said stomach wall.

9. An anti reflux system according to claim 8 wherein the distensible element is adapted to clamp the anti reflux device between the stomach wall and the distensible element.

10. An anti reflux system according to claim 9 wherein the positioning means comprises a tether detachably engageable with the distensible element to allow the distensible element to be drawn against the stomach wall.

11. An anti reflux system according to claim 9 wherein the distensible element is an inflatable balloon.

12. An anti reflux system according to claim 8 further comprising insertion means comprising an elongate tube adapted to receive the anti reflux device in a collapsed state, and from which tube the anti reflux device may be dispensed into the stomach.

\* \* \* \* \*